United States Patent
Yi et al.

(10) Patent No.: US 12,208,280 B2
(45) Date of Patent: *Jan. 28, 2025

(54) LASER DEVICE FOR SKIN TREATMENT CAPABLE OF ADJUSTING WAVELENGTH OF DIODE LASER AND/OR DURATION OF PULSE

(71) Applicant: JEISYS MEDICAL INC., Seoul (KR)

(72) Inventors: Won Ju Yi, Gwangmyeong-si (KR); Joo Hee Cho, Gunpo-si (KR); Seong Jun Kim, Gumi-si (KR); Min Young Kim, Incheon (KR); Dong Hwan Kang, Incheon (KR)

(73) Assignee: Jeisys Medical Inc., Seoul (KR)

( * ) Notice: Subject to any disclaimer, the term of this patent is extended or adjusted under 35 U.S.C. 154(b) by 1104 days.

This patent is subject to a terminal disclaimer.

(21) Appl. No.: 17/047,687

(22) PCT Filed: Jun. 30, 2020

(86) PCT No.: PCT/KR2020/008495
§ 371 (c)(1),
(2) Date: Oct. 14, 2020

(87) PCT Pub. No.: WO2021/020744
PCT Pub. Date: Feb. 4, 2021

(65) Prior Publication Data
US 2023/0124345 A1    Apr. 20, 2023

(30) Foreign Application Priority Data

Jul. 30, 2019 (KR) .................. 10-2019-0092454
Jul. 30, 2019 (KR) .................. 10-2019-0092455

(51) Int. Cl.
*A61N 5/06*    (2006.01)
*A61N 5/067*   (2006.01)

(52) U.S. Cl.
CPC ........... *A61N 5/067* (2021.08); *A61N 5/0616* (2013.01); *A61N 2005/0626* (2013.01);
(Continued)

(58) Field of Classification Search
CPC ........... A61B 18/20; A61N 5/06; A61F 9/008
See application file for complete search history.

(56) References Cited

U.S. PATENT DOCUMENTS

2009/0097507 A1* 4/2009 Zhu ................ H01S 3/1312
                                                    372/6
2020/0295524 A1* 9/2020 Magnano ............ H01S 3/106

FOREIGN PATENT DOCUMENTS

KR    10-2012-0108624 A    10/2012
KR       10-1576870 B1     12/2015
(Continued)

OTHER PUBLICATIONS

RP Photonics "Laser Gain Medium" (https://www.rp-photonics.com/laser_gain_media.html).*
(Continued)

*Primary Examiner* — Lynsey C Eiseman
(74) *Attorney, Agent, or Firm* — Leydig, Voit & Mayer, Ltd.

(57) ABSTRACT

A laser device for skin treatment, includes: a laser generating unit including one or a plurality of diode lasers configured to generate a diode laser pulse, one or a plurality of diode laser drivers each arranged to correspond to the diode laser and configured to vary diode laser pulses generated from the diode laser into pulses having different durations, a laser amplifying unit configured to amplify the pulse transmitted from the diode laser generating unit, and a controller configured to control the diode laser generating unit and the laser amplifying unit to control a wavelength and intensity of a laser output from the laser amplifying unit.

9 Claims, 6 Drawing Sheets

(52) U.S. Cl.
CPC ............... *A61N 2005/0652* (2013.01); *A61N 2005/0658* (2013.01); *A61N 2005/0666* (2013.01)

(56) References Cited

FOREIGN PATENT DOCUMENTS

| KR | 10-1599273 B1 | 3/2016 |
| KR | 10-1861286 B1 | 5/2018 |
| KR | 10-1898632 B1 | 9/2018 |

OTHER PUBLICATIONS

RP Photonics "Gain Bandwidth" (https://www.rp-photonics.com/gain_bandwidth.html).*
RP Photonics "Wavelength Tuning" (https://www.rp-photonics.com/wavelength_tuning.html).*

* cited by examiner

LASER DEVICE FOR SKIN TREATMENT CAPABLE OF ADJUSTING WAVELENGTH OF DIODE LASER AND/OR DURATION OF PULSE

TECHNICAL FIELD

The present invention relates to a laser device for skin treatment capable of adjusting a wavelength of a diode laser and/or duration of a pulse, and more particularly, to a laser device for skin treatment, including a laser generating unit capable of easily adjusting a wavelength of a diode laser and/or duration of a pulse so that the wavelength and the duration of the pulse can be adjusted.

BACKGROUND ART

Recently, research on a field using lasers is being actively conducted in the industry and research sites. In particular, these lasers have recently been briskly developed in research fields such as spectroscopy, nano-imaging, particle acceleration, and nuclear fusion, as well as life sites such as three-dimensional (3D) printing, roughening, and communication performances, and industrial sites such as welding, cutting, and surface modification.

These lasers are required to have different wavelengths depending on the intended use. However, existing lasers have a problem that requires an expensive wavelength conversion device to generate lasers having various wavelengths.

In addition, these lasers are required to vary the duration of a pulse and the wavelength and intensity of the laser according to the intended use. However, a laser device according to the related art has a problem that requires expensive or complex equipment so as to vary the duration of the pulse, the wavelength and the intensity of the laser.

DETAILED DESCRIPTION OF THE INVENTION

Technical Problem

The present invention provides a laser device for skin treatment, including a laser generating unit capable of easily adjusting a wavelength of a diode laser and/or duration of a pulse so that the wavelength and the duration of the pulse can be adjusted.

Technical Solution

According to an aspect of the present invention, there is provided a laser device for skin treatment, including a diode laser generating unit configured to vary at least one of a wavelength of a laser and duration of a pulse to generate a diode laser pulse, a laser amplifying unit configured to amplify the diode laser pulse transmitted from the diode laser generating unit, and a controller configured to control the diode laser generating unit and the laser amplifying unit to control at least one of the wavelength of the laser and the duration of the pulse output from the laser amplifying unit.

Effects of the Invention

A laser device for skin treatment capable of adjusting a wavelength of a diode laser and duration of a pulse according to the present invention has the following effects.

Firstly, by adjusting an operating temperature of a diode laser or a current value applied to the diode laser, the wavelength of a laser generated by a laser generating unit can be conveniently varied, and a pulse having adjusted duration can be output through a laser driver.

Secondly, a laser pulse having different types of wavelengths can be output without replacement of an amplification medium using a plurality of diode lasers.

Thirdly, a structure is simple so that the risk of failure or an operation error is small.

Fourthly, since a varied laser pulse can be conveniently generated, a pulse having various pulse durations can be output to a skin treatment target. In particular, the structure of a laser amplifying unit is very simple so that the pulse can be easily amplified.

Fifthly, the wavelength of a laser generated by a laser generating unit is varied by changing the temperature or current so that expensive equipment is not required and thus the laser device for skin treatment can be manufactured inexpensively.

Sixthly, since the wavelength can be varied by a wavelength varying unit in various ways, a laser pulse having various wavelengths can be output to the skin treatment target. In particular, the structure of the laser amplifying unit is very simple so that the pulse can be easily amplified.

MODE OF THE INVENTION

Figure 1:
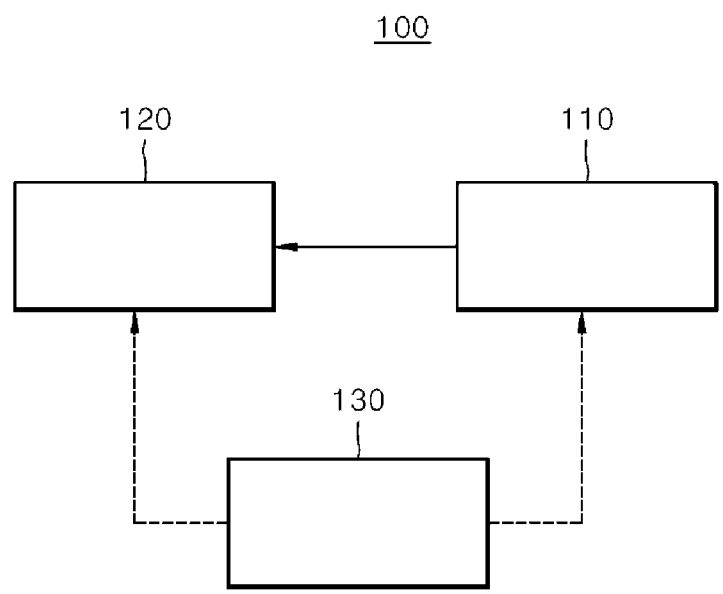
FIG. 1 is a schematic view of a laser device for skin treatment capable of adjusting a wavelength of a diode laser and duration of a pulse according to an embodiment of the present invention.
Figure 2:
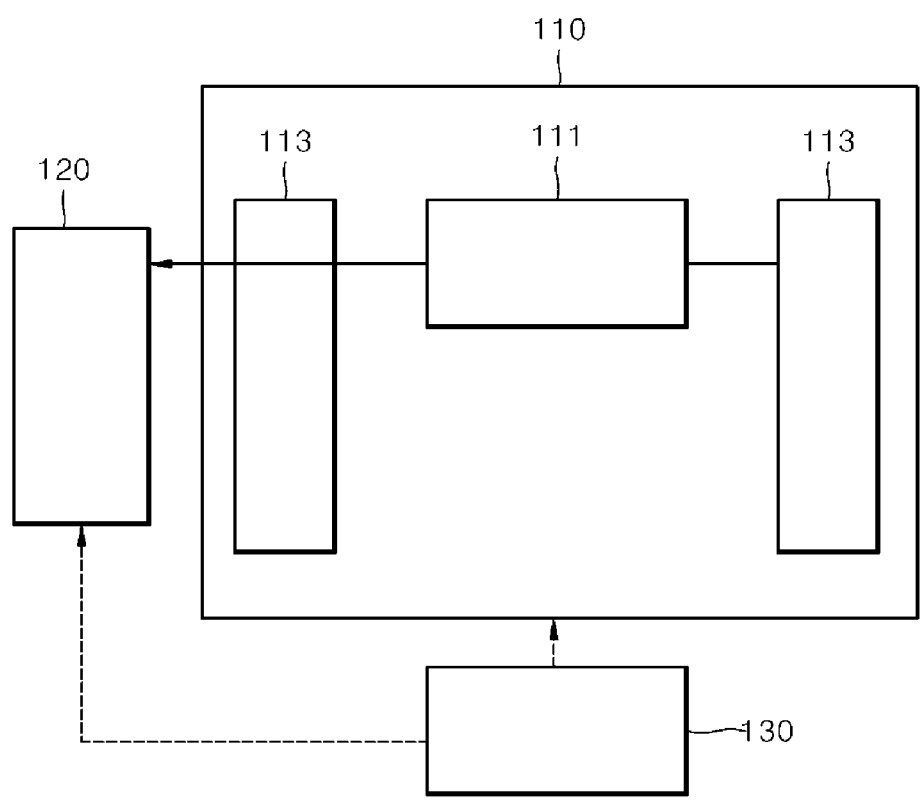
FIG. 2 is a schematic view schematically illustrating a diode laser generating unit of a laser device for skin treatment capable of adjusting a wavelength of a diode laser and duration of a pulse shown in FIG. 1.

Hereinafter, exemplary embodiments of the present invention will be described with reference to the accompanying drawings.

Referring to FIGS. 1 through 5, a laser device for skin treatment 100 according to an embodiment of the present invention includes a diode laser generating unit 110, a laser amplifying unit 120, and a controller 130. The diode laser generating unit 110 includes a laser generating unit 111 and a wavelength varying unit 113. The laser generating unit 111 includes a diode laser driver 111a and a diode laser 111b. The diode laser 111b emits a seed laser. That is, the diode laser 111b is formed as a light source that generates a pulse to be a source of a laser to be amplified by the laser amplifying unit 120 and to be output. A laser pulse generated by the diode laser 111b is controlled by the diode laser driver 111a.

In the present embodiment, the diode laser generating unit 110 includes only one laser generating unit 111 but may further include another laser generating unit (not shown). Hereinafter, an existing laser generating unit 111 is referred to as a first laser generating unit 111, and another laser generating unit is referred to as a second laser generating unit. In this case, the first laser generating unit 111 includes a first diode laser 111b and a first diode laser driver 111a. The second laser generating unit includes a second diode laser and a second diode laser driver. Of course, the laser generating unit 111 may include one diode laser and a plurality of diode laser drivers.

The first diode laser 111b and the second diode laser generate diode laser pulses having different wavelengths. The wavelength of a laser emitted from the laser amplifying unit 120 may vary according to the wavelength of the laser transmitted from the laser generating unit 110. Thus, wavelengths of the first diode laser 111b and the second diode laser are different from each other so that an output wavelength of the laser pulse emitted from the laser amplifying unit 120 can be changed. Thus, the laser device for skin treatment 100 according to the present embodiment may select any one of the first diode laser 111b and the second diode laser having different wavelengths, thereby conveniently adjusting an output wavelength.

Of course, the wavelengths of the first diode laser 111b and the second diode laser have a difference in a degree that falls within a range in which amplification is possible in an amplification medium included in the laser generating unit 120. That is, a difference in the wavelengths of the first diode laser 111b and the second diode laser falls within a range in which amplification is possible in one amplification medium. In detail, for example, when the amplification medium included in the laser generating unit 120 is Nd:YAG, it means that each of wavelengths of lasers generated in the first diode laser 111b and the second diode laser falls within a wavelength range in which amplification is possible with Nd:YAG. However, the present invention is not limited thereto, and a diode laser pulse having the same wavelength may be generated in the first diode laser 111b and the second diode laser.

As above, the laser generating unit 110 may include two individual diode lasers, i.e., the first diode laser 111b and the second diode laser, however, the number of individual diode lasers included in the laser generating unit 110 may be changed as much as possible. The first diode laser 111b and the second diode laser may generate a laser pulse through on/off control.

Figure 3:
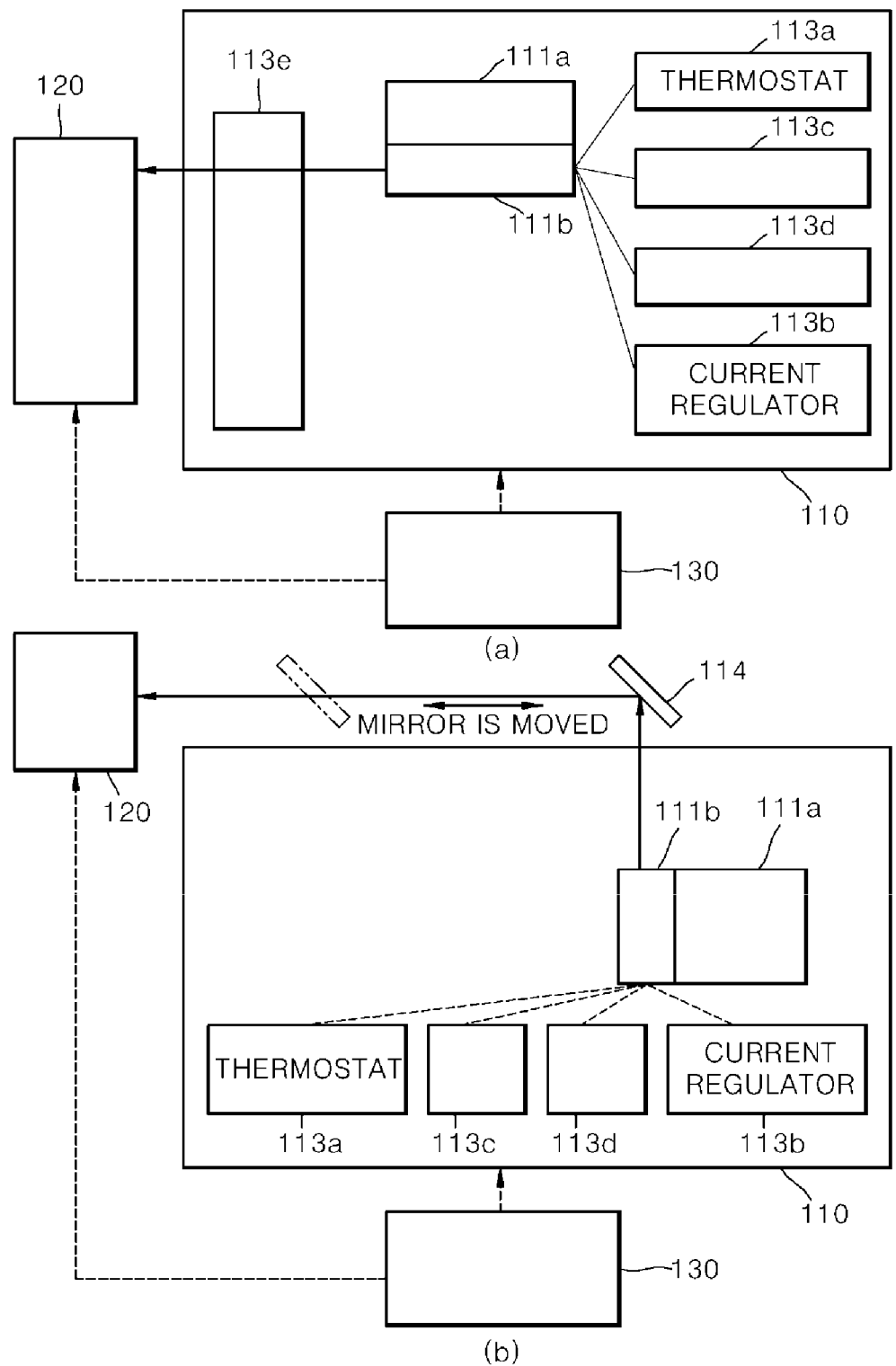
FIG. 3 is a schematic view specifically illustrating a diode laser generating unit of a laser device for skin treatment capable of adjusting a wavelength of a diode laser and duration of a pulse shown in FIG. 1.

Referring to (a) of FIG. 3, the first laser generating unit 111 includes a first diode laser driver 111a and a first diode laser 111b. The first diode laser driver 111a controls the first diode laser 111b to generate a variable laser pulse having variable pulse duration. The duration of the diode laser generated from the first diode laser 111b is formed from first duration to second duration. For example, the laser pulse generated by the first laser generating unit 111 is formed in picoseconds (ps) or nanoseconds (ns).

Although not shown, the second diode laser driver controls the second diode laser to generate a variable laser pulse having variable pulse duration. The duration of the diode laser pulse generated from the second diode laser may be formed from third duration to fourth duration. At this time, the laser pulse generated by the second laser generating unit has longer duration than that of a laser pulse generated by the first laser generating unit 111. That is, the third duration and the fourth duration may be longer than the first duration and the second duration. For example, the laser pulse generated by the second laser generating unit is formed in ns or ps. At this time, even if it falls within the same ns range, the duration of the laser pulse in the range of ns generated by the second laser generating unit is longer than that of the laser pulse in the range of ns generated by the first laser generating unit 111. Of course, the duration of the laser pulse each generated by the first laser generating unit 111 and the second laser generating unit may be changed as much as possible through driver replacement.

The first diode laser driver 111a controls the first diode laser 111b to adjust the laser pulse generated from the first diode laser 111b in ps or ns and to emit the laser pulse sequentially with a time difference. The second diode laser driver controls the second diode laser to adjust the laser pulse generated from the second diode laser in ns or ms and to emit the laser pulse sequentially with a time difference. At this time, the laser pulses sequentially emitted from the first diode laser 111b and the second diode laser are transmitted to the laser amplifying unit 120.

(b) of FIG. 3 illustrates another structure of the diode laser generating unit 110. Although (b) is almost similar to the case of (a), there is a difference in the path of a laser pulse emitted from the first laser generating unit 111. That is, there is a difference between (b) and (a) of FIG. 3 in that the laser pulse emitted from the first laser generating unit 111 is directly transmitted to the laser amplifying unit 120 or is transmitted to the laser amplifying unit 120 after the path of the laser pulse is adjusted by the ninth mirror 114. Also, although not shown, when the second laser generating unit is installed, (b) is different from (a) in that, unlike in (a), the laser pulses emitted from the first laser generating unit 111 and the second laser generating unit are transmitted to the laser amplifying unit 120 on the same path. This difference occurs due to the ninth mirror 114 that adjusts the paths of the laser pulses emitted from the first laser generating unit 111 and the second laser generating unit. That is, the ninth mirror 114 may adjust the paths of the laser pulses generated by the first laser generating unit 111 to be transmitted to the laser amplifying unit 120 on the same path. Of course, the ninth mirror 114 transmits the laser pulses generated by the laser generating units 111 that emit laser pulses having wavelengths capable of being amplified according to the type of an amplification medium arranged on the laser amplifying unit 120, to the laser amplifying unit 120. At this time, the ninth mirror 114 is moved in forward and down directions or left and right directions so as to transmit the laser pulse generated by the first laser generating unit 111 or the second laser generating unit to the laser amplifying unit 120. The ninth mirror 114 is moved by a motor controlled by the controller 130. In the present embodiment, the ninth mirror 114 is one, and when the ninth mirror 114 is moved, the paths of the laser pulses generated by the first laser generating unit 111 and the second laser generating unit are changed. However, a plurality of the ninth mirrors 114 may be fixed and installed according to the number of diode lasers.

At this time, when the diode laser generating unit 110 includes only the first laser generating unit 111, the laser pulse generated by the first diode laser 111b is adjusted in ps or ns and is emitted. When the diode laser generating unit 110 includes the second laser generating unit, the laser pulse generated by the second diode laser may be adjusted in ns or ms and emitted.

Even when the laser generating unit 110 includes the first laser generating unit 111 and the second laser generating unit, only one of the first laser generating unit 111 and the second laser generating unit operates to emit only the pulse in ps or ns or so that only the pulse in ps or ns may be emitted or only the pulse in ns or ms can be emitted. That is, only one of the first laser generating unit 111 and the second laser generating unit operates so that the same effect as that only one of the first laser generating unit 111 and the second laser generating unit is installed in the laser generating unit 110, can be produced.

Figure 4:
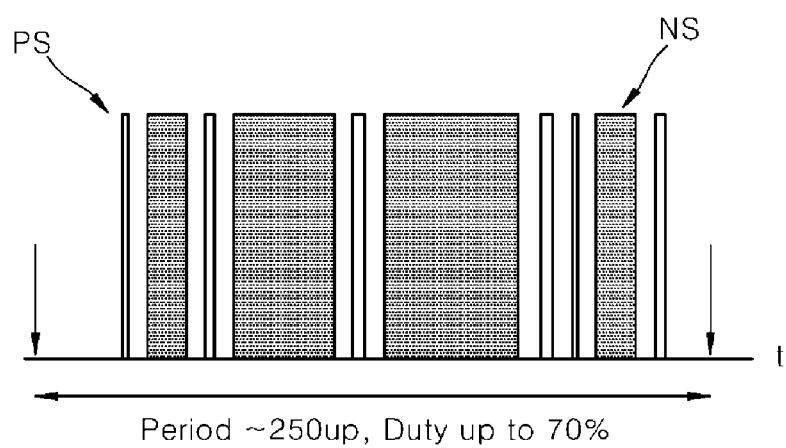
FIG. 4 is a schematic view of a pulse generated by a diode laser generating unit of a laser device for skin treatment capable of adjusting a wavelength of a diode laser and duration of a pulse shown in FIG. 1.

Referring to FIG. 4, the first diode laser driver 111a controls the first diode laser 111b, and the second diode laser driver controls the second diode laser so that a certain variable laser pulse having variable pulse duration can be formed. The duration of the diode laser pulse generated from the first diode laser 111b is controlled by the first diode laser driver from the first duration to the second duration. The duration of the diode laser pulse generated from the second diode laser is controlled by the second diode laser driver from the third duration to the fourth duration. At this time, the variable laser pulse that is controlled by the second diode laser driver and generated from the second diode laser is controlled by the first diode laser driver 111a and has longer duration than the variable laser pulse generated from the second diode laser. That is, the third duration and the fourth duration are longer than the first duration and the second duration. Of course, the duration of the laser pulse generated from the first diode laser 111b and the second diode laser may be changed by diode laser drivers as much as possible.

In detail, the first diode laser driver 111a may generate a laser pulse in the wavelength range of 100 ps or more and 10 ns or less, and the second diode laser driver may generate a laser pulse in the wavelength of 10 ns or more and 10 ms or less. That is, the duration of the variable laser pulse may be formed in 100 ps to 10 ms. In the present embodiment, the duration of the variable laser pulse is 100 ps to ms. However, the duration of the variable laser pulse may be changed as much as possible by changing the diode laser drivers.

Also, the duration of the variable laser pulse may belong to only the range of ps or only the range of ns, or both the ranges of ps and ns. That is, the duration of the variable laser pulse may be formed to belong to only one time unit or may be formed to include several time ranges. The variable laser pulse may change the diode laser drivers so that the duration of the laser pulse generated from the first diode laser 111b and the second diode laser can be variously adjusted.

The pulse generated from the first diode laser 111b and the second diode laser may be varied with a pulse width of 100 ps to several ms. The pulse width of the laser pulse generated from the first diode laser 111b and the second diode laser may be adjusted according to an input signal of the controller 130.

The wavelength varying unit 113 includes a thermostat 113a, a current regulator 113b, a temperature sensor 113c, a current sensor 113d, and a wavelength detection sensor 113e. The thermostat 113a may control the temperature of the first diode laser 111b to adjust the wavelength of the laser generated from the first diode laser 111b. That is, the temperature of the laser pulse generated from the first diode laser 111b by using the thermostat 113a may be changed by 1° C. so that the wavelength of the laser can be changed in the range of 0.05 nm to 0.3 nm. However, the present invention is not limited thereto, and the change range of the wavelength with respect to the temperature change of 1° C. may be changed according to the characteristics of the diode. The thermostat 113a may include a heater (not shown) and a cooler (not shown) connected to the first diode laser 111b. The heater may be formed as an electrode, and the cooler may be formed as a fan. Of course, this is exemplary, and the configuration of the thermostat 113a may be changed as much as possible. The temperature sensor 113c measures the temperature of the first diode laser 111b and the second diode laser and transmits measured information to the controller 130. This is to accurately predict the wavelength of the laser output by measuring the correct temperature of the first diode laser 111b.

The current regulator 113b adjusts a current applied to the first diode laser 111b to adjust the wavelength of the laser generated from the first diode laser 111b. The current of the laser pulse generated from the first diode laser 111b is changed by 1 ampere (A) by using the current regulator 113b so that the wavelength of the laser is changed in the range of 0.05 nm to 1 nm. However, the present invention is not limited thereto, and the change range of the wavelength with respect to the current change of 1 A may be changed according to the characteristics of the diode. The current regulator 113b may be formed as an electrode that is connected to the first diode laser 111b and supplies a current. Of course, the configuration of the current regulator 113b may be changed as much as possible. The current sensor 113d measures the current applied to the first diode laser 111b and transmits measured information to the controller 130. This is to accurately predict the wavelength of a laser output by measuring the correct current applied to the first diode laser 111b.

The thermostat 113a and the current regulator 113b may individually operate or simultaneously. In the present embodiment, the thermostat 113a and the current regulator 113b are separate configurations. However, the temperature thermostat 113a and the current regulator 113b may be formed as one configuration to adjust both the temperature and the current. When the amplification medium included in the laser amplifying unit 120 is neodymium:gadolinium gallium garnet (Nd:GGG), the thermostat 113a and the current regulator 113b adjust the temperature or current so that the laser pulse having the wavelength in the range of 1062 nm to 1067 nm may be generated, and when the amplification medium included in the laser amplifying unit 120 is ytterbium (3+): LaCa4O (BO3) 3 (Yb:LaCOB), the thermostat 113a and the current regulator 113b adjust the temperature or current so that the laser pulse having the wavelength in the range of 1029 nm to 1042 nm may be generated. Of course, the thermostat 113a and the current regulator 113b may adjust both the temperature and the current. However, the amplification medium and the wavelength range adjusted according to the amplification medium are exemplary and may be changed variously.

The wavelength detection sensor 113e measures the wavelength of the laser generated from the first diode laser 111b. This is to check whether the wavelength of the laser pulse generated from the first diode laser 111b is properly adjusted by the thermostat 113a and the current regulator 113b. When the wavelength of the first diode laser 111b as a result of checking is properly adjusted to the wavelength in a desired range, the laser pulse generated from the first diode laser 111b is transmitted to the laser amplifying unit 120 as it is. However, when the wavelength of the first diode laser 111b is not properly adjusted to the wavelength in the desired range, information on the wavelength detected by the wavelength detection sensor 113e is transmitted to the controller 130, and the controller 130 adjusts the wavelength of the first diode laser 111b again by operating the thermostat 113a and the current regulator 113b. In the present embodiment, although the wavelength detection sensor 113e is separately installed in the wavelength varying unit 113, the wavelength detection sensor 113e may not be installed in the varying unit 113. That is, since a database on an operating temperature and an applied current is configured in the wavelength varying unit 113, the thermostat 113a and the current regulator 113b may be adjusted using the database so that the wavelength may be adjusted. However, when the wavelength detection sensor 113e is further installed, the wavelength can be more accurately detected and adjusted.

The laser amplifying unit 120 includes a first beam splitter 123, a first amplification medium 121a, a first mirror 122a, a first wave plate 124, a second mirror 122b, a second amplification medium 121b, a third mirror 122c, a fourth mirror 122d, a third amplification medium 121c, a fifth mirror 122e, a sixth mirror 122f, a fourth amplification medium 121d, a seventh mirror 122g, an eighth mirror 122h, a first lens 125a, a second lens 125b, a first pumping lamp 126a, and a second pumping lamp 126b. The first beam splitter 123 transmits a P-polarization and reflects an S-polarization. Thus, since the laser pulse supplied from the laser generating unit 110 is a P-wave, the laser pulse transmits the first beam splitter 123 as it is. Also, the first beam splitter 123 is arranged on the same axis as the proceeding direction of the laser pulse supplied from the laser generating unit 110. Of course, the arrangement of the first beam splitter 123 may be changed. Another role of the first beam splitter 123 will be described later.

The first amplification medium 121a serves to amplify the laser pulse supplied from the laser generating unit 110 while the laser pulse passes through the first amplification medium 121a a single or multiple times. The first pumping lamp 126a illuminates the first amplification medium 121a so as to excite ions in the first amplification medium 121a. The first pumping lamp 126a is spaced apart from the first amplification medium 121a. The first amplification medium 121a is formed in a rod structure. The first amplification medium 121a is formed of neodymium:yttrium aluminum garnet (Nd:YAG) or paraseodymium:yttrium lithium fluoride (Pr:YLF). For example, when the wavelength of the laser supplied from the laser generating unit 110 is 946 nm, 1064 nm or 1319 nm, the first amplification medium 121a is formed of Nd:YAG. When the wavelength of the laser supplied from the laser generating unit 110 is 523 nm, 607 nm or 640 nm, the first amplification medium 121a is formed of Pr:YLF. However, in the present invention, the first amplification medium 121a may be changed into other types as much as possible.

The first amplification medium 121a is arranged on the same axis as the first beam splitter 123. Thus, the laser pulse passing through the first beam splitter 123 is first amplified while passing through the first amplification medium 121a.

The first mirror 122a is arranged on the same axis as the first beam splitter 123 and the first amplification medium 121a. Thus, the first mirror 122a is a total reflection mirror that reflects the laser pulse first amplified while passing through the first amplification medium 121a in a direction of the first amplification medium 121a. The first mirror 122a returns the laser pulse that is first amplified while passing through the first amplification medium 121a to amplify the laser pulse by the first amplification medium 121a again.

In this case, a first wave plate 124 is arranged between the first amplification medium 121a and the first mirror 122a. The first wave plate 124 is formed as a quarter-wave-plate (QWP) that changes the phase of a wave passing through the first wave plate 124 by ¼ wavelength. That is, the first wave plate 122c changes the phase of the laser pulse directed to the first mirror 122a by passing through the first amplification medium 121a by ¼ wavelength and changes the phase of the laser pulse reflected from the first mirror 122a and returning to the first amplification medium 121a by ¼ wavelength again. Thus, the p-wave supplied from the laser generating unit 110 passes through the first wave plate 124 twice and is changed into an s-wave. This is to change the proceeding path of the laser pulse by reflecting rather than transmitting when returning to the first beam splitter 123.

The laser pulse that returns to the first amplification medium 121a again after passing the first wave plate 124 twice passes through the first amplification medium 121a and is second amplified. The path of the second amplified laser pulse is adjusted by the first beam splitter 123. That is, the second amplified laser pulse is reflected by the first beam splitter 123, and the path of the second amplified laser pulse is changed by 90 degrees.

The second mirror 122b is formed above the first beam splitter 123. Thus, the laser pulse reflected by the first beam splitter 123 is reflected from the second mirror 122b. The second mirror 122b is arranged in such a way that the laser pulse supplied from the first beam splitter 123 may be reflected in a direction of the second amplification medium 121b.

The second amplification medium 121b serves to third amplify the laser pulse reflected from the second mirror 122b. The second amplification medium 121b is spaced apart from the first amplification medium 121a. Ions in the second amplification medium 121b may be excited by the first pumping lamp 126b. The second amplification medium 121b is formed in a rod structure. Also, the second amplification medium 121b is formed of Nd:YAG or Pr:YLF. For example, when the wavelength of the laser supplied from the laser generating unit 110 is 946 nm, 1064 nm or 1319 nm, the second amplification medium 121b is formed of Nd:YAG. Also, when the wavelength of the laser supplied from the laser generating unit 110 is 523 nm, 607 nm or 640 nm, the second amplification medium 121b is formed of Pr:YLF. However, the present invention is not limited thereto, and the second amplification medium 121b may be changed into Nd:GGG or Yb:LaCOB, or other types as much as possible.

Also, the second amplification medium 121b is arranged above the first amplification medium 121a. Also, the second amplification medium 121b is arranged on the same axis as the second mirror 122b. That is, the second amplification medium 121b may also be arranged below the first amplification medium 121a according to the arrangement location of the second mirror 122b.

The third mirror 122c is arranged to face the second mirror 122b with the second amplification medium 121b therebetween. The third mirror 122c reflects the third amplified laser pulse while passing through the second amplification medium 121b and adjusts the path of the third amplified laser pulse. That is, the third mirror 122c serves to reflect the laser pulse passing through the second amplification medium 121b so that the path of the laser pulse may be changed by 90 degrees. Of course, the reflection angle of the laser pulse reflected from the third mirror 122c may be changed. The third mirror 122c is also arranged on the same axis as the second mirror 122b and the second amplification medium 121b.

The fourth mirror 122d reflects the laser pulse supplied from the third mirror 122c in a direction of the third amplification medium 121c. In this case, the proceeding path of the laser pulse directed to the fourth mirror 122d from the third mirror 122c may further include lens units 125a and 125b for adjusting the spatial size of the laser pulse. The lens units 125a and 125b may include a first lens 125a and a second lens 125b. The lens units 125a and 125b may adjust a distance between the first lens 125a and the second lens 125b to adjust the spatial size of the laser pulse directed to the fourth mirror 122d from the third mirror 122c.

The third amplification medium 121c serves to fourth amplify the laser pulse reflected from the fourth mirror 122b. The third amplification medium 121c is spaced apart from the fourth amplification medium 121d. Ions in the third amplification medium 121c may be excited by the second pumping lamp 126b. The third amplification medium 121c is formed in a rod structure. The third amplification medium 121c is formed of Nd:YAG or Pr:YLF. For example, when the wavelength of the laser supplied from the laser generating unit 110 is 946 nm, 1064 nm or 1319 nm, the third amplification medium 121c is formed of Nd:YAG. Also, when the wavelength of the laser supplied from the laser generating unit 110 is 523 nm, 607 nm or 640 nm, the third amplification medium 121c is formed of Pr:YLF. However, the present invention is not limited thereto, and the third amplification medium 121c may be changed into Nd:GGG or Yb:LaCOB, or other types as much as possible.

The fifth mirror 122e is arranged to face the fourth mirror 125b with the third amplification medium 121c therebetween. The fifth mirror 122e reflects the fourth amplified laser pulse while passing through the third amplification medium 121c and adjusts the path of the fourth amplified laser pulse. That is, the fifth mirror 122e serves to reflect the laser pulse passing through the third amplification medium 121c to change the path of the laser pulse by 90 degrees. Of course, the reflection angle of the laser pulse reflected from the fifth mirror 122e may be changed. The fifth mirror 122e is arranged on the same axis as the fourth mirror 122d and the third amplification medium 121c.

The sixth mirror 122f reflects the laser pulse supplied from the fifth mirror 122e in a direction of the fourth amplification medium 121d. In the present embodiment, the sixth mirror 122f is formed separately from the fifth mirror 122e, but the fifth mirror 122e and the sixth mirror 122f may be formed as one mirror.

The fourth amplification medium 121d serves to fifth amplify the laser pulse reflected from the sixth mirror 122f. The fourth amplification medium 121d is spaced apart from the third amplification medium 121c. Ions in the fourth amplification medium 121d may be excited by the second pumping lamp 126d. The fourth amplification medium 121d is formed in a rod structure. The fourth amplification medium 121d is formed of Nd:YAG or Pr:YLF. For example, when the wavelength of the laser supplied from the laser generating unit 110 is 946 nm, 1064 nm or 1319 nm, the fourth amplification medium 121d is formed of Nd:YAG. Also, when the wavelength of the laser supplied from the laser generating unit 110 is 523 nm, 607 nm or 640 nm, the fourth amplification medium 121d is formed of Pr:YLF. However, the present invention is not limited thereto, and the fourth amplification medium 121d May be changed into Nd:GGG or Yb:LaCOB, or other types as much as possible.

The seventh mirror 122g is arranged to face the sixth mirror 122f with the fourth amplification medium 121d therebetween. Also, the seventh mirror 122g reflects the laser pulse passing through the fourth amplification medium 121d to adjust the path of the laser pulse in a direction of the eighth mirror 122h.

The eighth mirror 122h is arranged on one side of the seventh mirror 122g and adjusts the path of the laser pulse supplied from the seventh mirror 122g. The laser pulse having the path adjusted by the eighth mirror 122h is output to the laser amplifying unit 120. However, the present invention is not limited thereto, and the laser pulse may be output to the laser amplifying unit 120 directly from the seventh mirror 122g.

Although not shown in the drawings, a second harmonic generator (SHG) (not shown) may be arranged to change the wavelength of the laser pulse output from the seventh mirror 122g or the eighth mirror 122h. The SHG (not shown) is arranged on a path on which the laser pulse output from the seventh mirror 122g or the eighth mirror 122h proceeds. The SHG (not shown) changes the wavelength of the laser pulse output from the eighth mirror 122h similarly to a known wavelength-changing method.

The controller 130 serves to control the laser generating unit 110 and the laser amplifying unit 120. That is, the controller 130 adjusts a wavelength and a pulse width of the laser generated by applying a signal to the laser source generating unit 111 and the pulse width adjustment unit. At this time, the controller 130 varies the pulse width by using the first diode laser driver 111a and the second diode laser driver 111b included in the laser generating unit 110. Since the first diode laser driver 111a and the second diode laser driver 111b have a short rising time of 100 ps or less, a pulse width control of several tens of ps is used. In the case of the first diode laser diode 111a and the second diode laser driver 111b, a driver for short pulses of ps or a driver for controlling pulses of ms or more may be selected and used. The controller 130 according to the present embodiment controls at least one of the wavelength of the laser output from the laser amplifying unit 120 and duration of a pulse output from the laser amplifying unit 120. That is, the controller 130 may control only the wavelength of the laser output from the amplifying unit 120, only the duration of the pulse output from the amplifying unit 120, or both the wavelength of the laser and the duration of the pulse output from the amplifying unit 120.

Also, the controller 130 may control the states of the first amplification medium 121a, the second amplification medium 121b, the third amplification medium 121c, and the fourth amplification medium 121d by applying signals to the first pumping lamp 126a and the second pumping lamp 126b of the laser amplifying unit 120. Also, the controller 130 may also control the laser pulse generated by transmitting the signal to the laser generating unit 110 when the laser pulse output by the laser amplifying unit 120 does not have a required energy level.

The controller 130 includes a database DB for storing information on the wavelength range in which amplification is possible, of the laser amplifying unit 120. That is, the database DB stores information on the wavelength range in which amplification is possible by the first amplification medium 121a, the second amplification medium 121b, the third amplification medium 121c and the fourth amplification medium 121d. Also, the database stores information on the wavelength that varies according to the adjusted temperature or current value when the wavelength varying unit 113 adjusts the operating temperature of the first laser generating unit 111 or the current value applied to the first laser generating unit 111. Thus, the laser device 100 for skin treatment according to the present embodiment stores both information on the wavelength that can be amplified by the laser amplifying unit 120 and information on the temperature and the current value for generating the laser pulse having the wavelength that can be amplified by the laser amplifying unit 120. Therefore, the laser pulse having a required wavelength can be conveniently generated by adjusting only the operating temperature of the first laser generating unit 111 or the current value applied to the first laser generating unit 111 based on the database so as to be matched with the wavelength that can be amplified by the laser amplifying unit 120.

The laser device for skin treatment 100 according to the present embodiment has a structure in which the wavelength and the pulse width can be conveniently varied by the laser generating unit 110 and the laser pulse generated by the laser generating unit 110 can be repeatedly amplified several times, so that the laser pulse with small energy generated by the laser generating unit 110 can be amplified to a laser pulse with large energy.

Figure 5:
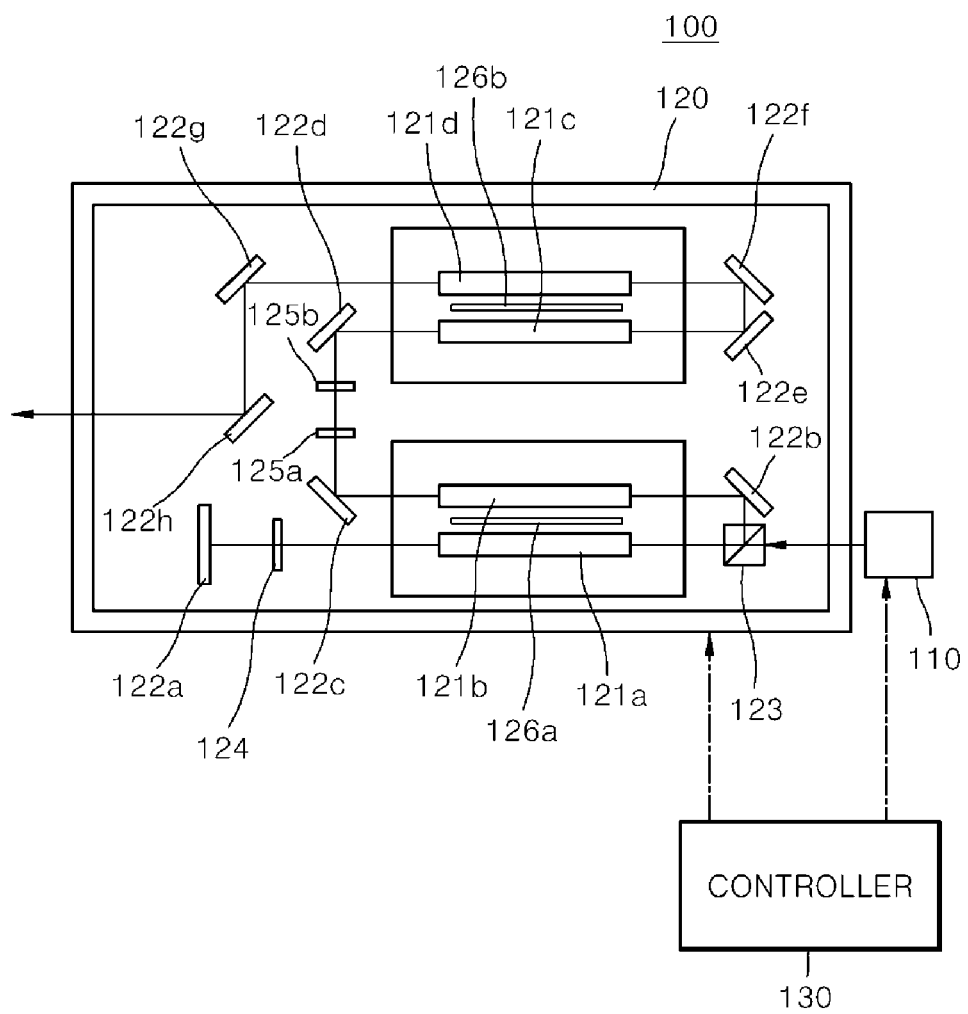
FIG. 5 is a schematic view specifically illustrating an amplifying unit of a laser device for skin treatment capable of adjusting a wavelength of a diode laser and duration of a pulse shown in FIG. 1.

In FIG. 5, one first pumping lamp 126a and one second pumping lamp 126b are arranged. However, the present invention is not limited thereto. Each of the first pumping lamp 126a and the second pumping lamp 126b has a structure including two lamps so that each lamp of the first pumping lamp 126a irradiates light to the first amplification medium 121a and the second amplification medium 121b and each of the second pumping lamp 126b irradiates light to the third amplification medium 121c and the fourth amplification medium 121d. Also, a lamp for illuminating each of the first amplification medium 121a, the second amplification medium 121b, the third amplification medium 121c, and the fourth amplification medium 121d may be separately arranged by one. In this case, the amplification pulse energy of the laser amplifying unit 120 further increases.

Figure 6:
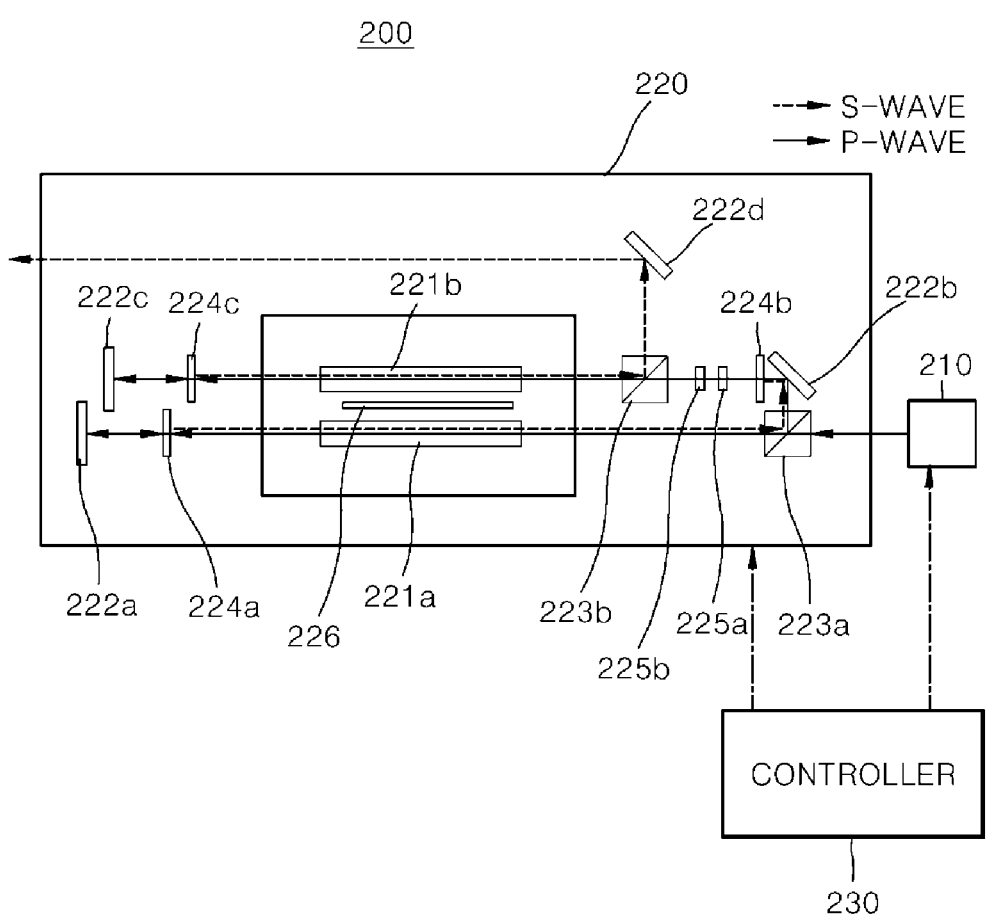
FIG. 6 is a schematic view of a laser device for skin treatment capable of adjusting a wavelength of a diode laser and duration of a pulse according to another embodiment of the present invention.

Referring to FIG. 6, a laser device for skin treatment 200 according to another embodiment of the present invention includes a laser generating unit 210, a laser amplifying unit 220, and a controller 230. In the laser device 200 for skin treatment according to the present embodiment, the laser generating unit 210 and the controller 230 are similar to the laser device for skin treatment 100 shown in FIG. 5 and thus, a description thereof will be omitted.

The laser amplifying unit 220 includes a first beam splitter 223a, a first amplification medium 221a, a first mirror 222a, a first wave plate 224a, a second mirror 222b, a second wave plate 224b, a second amplification medium 221b, a first pumping lamp 226, a third mirror 222c, a second beam splitter 223b, a third wave plate 224c, a first lens 225a, a second lens 225b, and a fourth mirror 222d. Although not shown, an SHG (not shown) as in the laser device for skin treatment 100 of FIG. 5 may be further included in the laser amplifying unit 220. The first beam splitter 223a transmits P-polarized light and reflects S-polarized light. Thus, the laser pulse supplied from the laser generating unit 210 is a P-wave as in the laser generating unit 110 shown in FIG. 3 and thus transmits the first beam splitter 223a as it is. Also, the first beam splitter 223a is arranged on the same axis as the proceeding direction of the laser source supplied from the laser generating unit 210. Of course, the arrangement of the first beam splitter 223a may be changed.

The first amplification medium 221a serves to amplify the laser source supplied from the laser generating unit 210. The first pumping lamp 226 illuminates the first amplification medium 221a so as to excite ions in the first amplification medium 221a. The first pumping lamp 226a is spaced apart from the first amplification medium 221a. The first amplification medium 221a is formed in a rod structure. The first amplification medium 221a is formed of Nd:YAG. However, the present invention is not limited thereto, and the first amplification medium 221a may be changed into Nd:GGG or Yb:LaCOB, other types, structures, and shapes as much as possible.

Also, the first amplification medium 221a is arranged on the same axis as the first beam splitter 223a. Thus, the laser pulse that transmits the first beam splitter 223a is first amplified while passing through the first amplification medium 221a.

The first mirror 222a is arranged on the same axis as the first beam splitter 223a and the first amplification medium 221a. Also, the first mirror 222a is arranged to face the first beam splitter 223a with the first amplification medium 221a therebetween. The first mirror 222a is a total reflection mirror that reflects the laser pulse first amplified while passing through the first amplification medium 221a in a direction of the first amplification medium 221a. The first mirror 222a serves to return the first amplified laser pulse while passing through the first amplification medium 221a to amplify it once again by the first amplification medium 121a.

At this time, the first wave plate 224a is arranged between the first amplification medium 221a and the first mirror 222a. The first wave plate 124 is formed as a QWP that changes the phase of a wave passing through the first wave plate 224a by ¼ wavelength. After passing through the first amplification medium 221a, the laser pulse directed to the first mirror 222a by passing through the first wave plate 224a and the laser pulse reflected from the first mirror 222a and directed to the first wave plate 224a are circularly polarized and proceed. That is, the first wave plate 224a changes the phase of the laser pulse directed to the first mirror 222a by passing through the first amplification medium 221a by ¼ wavelength and changes the phase of the laser pulse reflected from the first mirror 222a and returning to the first amplification medium 221a by ¼ wavelength again. Thus, the P-wave supplied from the laser generating unit 210 passes through the first wave plate 224a twice and is changed into an S-wave. This is to change the proceeding path of the laser pulse by reflecting rather than transmitting when returning to the first beam splitter 223a.

The laser pulse that returns to the first amplification medium 221a again after passing through the first wave plate 224a twice is second amplified while passing through the first amplification medium 221a. The path of the second amplified laser pulse is adjusted by the first beam splitter 223a. That is, the second amplified laser pulse is reflected by the first beam splitter 223a, and the path of the second amplified laser pulse is changed by 90 degrees.

The second mirror 222b is arranged on one side in which the path of the first beam splitter 223a is changed by 90 degrees. Thus, the laser pulse reflected by the first beam splitter 223a is reflected from the second mirror 222b. The second mirror 222b is arranged in such a way that the laser pulse supplied from the first beam splitter 223a may be reflected in a direction of the second amplification medium 221b.

The second wave plate 224b changes the phase of the laser pulse that is reflected from the second mirror 222b and directed to the second amplification medium 221b. At this time, the second wave plate 224b is formed as a half wave plate (HWP), unlike in the first wave plate 224a. That is, the laser pulse supplied to the second wave plate 224b is an S-wave, and the laser pulse that passes through the second wave plate 224b changes the phase of the wave by ½ wavelength, resulting in a P-wave. This is to allow the laser pulse reflected from the second mirror 224b to transmit the second beam splitter 223b located to face the second mirror 224b with the second wave plate 224b therebetween.

The second beam splitter 223b is arranged between the second wave plate 224b and the second amplification medium 221b. Since the laser pulse passing through the second wave plate 224b is a P-wave, the second beam splitter 223b transmits the laser pulse rather than reflects it.

The first lens 225a and the second lens 225b are arranged between the second beam splitter 223b and the second wave plate 224b. The first lens 225a and the second lens 225b adjust the spatial size of the laser pulse reflected from the second mirror 222b.

The second amplification medium 221b serves to third amplify the laser pulse supplied by transmitting the second beam splitter 223b. The first pumping lamp 226 illuminates the second amplification medium 221b so as to excite ions in the second amplification medium 221b. The first pumping lamp 226 is spaced apart from the second amplification medium 221b. The second amplification medium 221b is formed as a rod structure. The second amplification medium 221b is formed of Nd:YAG. However, the present invention is not limited thereto and may be changed into Nd:GGG or Yb:LaCOB, other types and structure as much as possible.

In the present invention, the first pumping lamp 226 illuminates both the first amplification medium 221a and the second amplification medium 221b. However, the present invention is not limited thereto, and the first pumping lamp 226 has a structure including two lamps so that each lamp of the first pumping lamp 226 illustrates the first amplification medium 221a and the second amplification medium 221b. Also, a lamp for illuminating each of the first amplification medium 221a and the second amplification medium 221b may be separately arranged by one. In this case, the amplification pulse energy of the laser amplifying unit 220 further increases.

The third mirror 222c serves to return to the second amplification medium 221b by reflecting the third amplified laser pulse while passing through the second amplification medium 221b. At this time, the third wave plate 224c is arranged between the third mirror 222c and the second amplification medium 221b. The third wave plate 224c is formed as a QWP, as in the first wave plate 224a. Thus, the phase of the laser pulse is changed by ¼ wavelength while the laser pulse proceeds to the third mirror 222c from the second amplification medium 221b, and when returning to the second amplification medium 221b from the third mirror 222c, the phase of the laser pulse is changed by ¼ wavelength. After passing through the second amplification medium 221b, the laser pulse directed to the third mirror 222c while passing through the third wave plate 224c and the laser pulse reflected from the third mirror 222c and directed to the third wave plate 224c are circularly polarized and proceed. That is, the waveform of the laser pulse returning to the second amplification medium 221b is changed from the P-wave to the S-wave.

The second beam splitter 223b reflects the laser pulse that is reflected from the third mirror 222c and is fourth amplified by passing through the second amplification medium 221b, to adjust the path of the laser pulse. The laser pulse having the path adjusted by being reflected by the second beam splitter 223b, is reflected by the fourth mirror 222d arranged on one side of the second beam splitter 223b and is output.

The laser device for skin treatment 200 according to the present embodiment has an advantage of having a simpler structure than the laser device for skin treatment 100 of FIG. 5, although the number of amplification times is four times that is less once compared to the laser device for skin treatment 100 of FIG. 1. Also, since there are four amplifications, it is possible to amplify low energy laser pulse generated by the laser generating unit 210 into a laser pulse having a sufficiently large energy.

Figure 7:
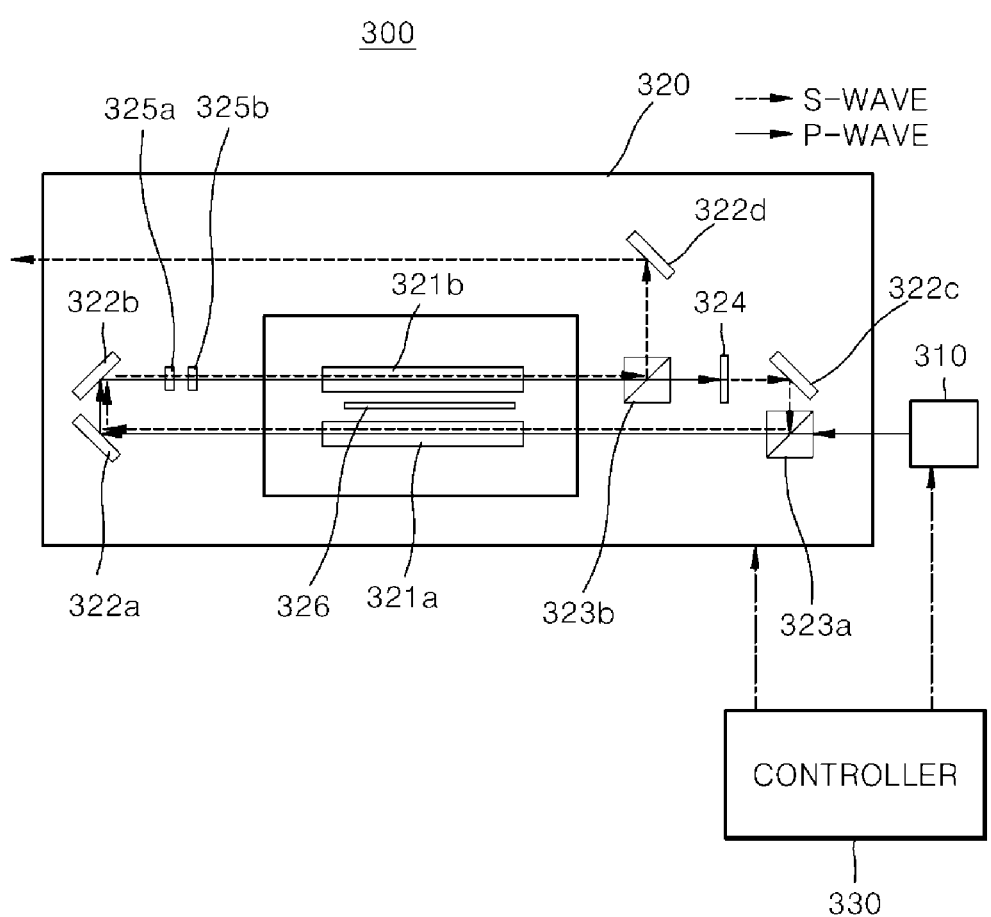
FIG. 7 is a schematic view of a laser device for skin treatment capable of adjusting a wavelength of a diode laser and duration of a pulse according to another embodiment of the present invention.

Referring to FIG. 7, a laser device for skin treatment 300 according to another embodiment of the present invention includes a laser generating unit 310, a laser amplifying unit 320, and a controller 330. The laser generating unit 310 and the controller 330 are similar to those of the laser device for skin treatment 100 shown in FIG. 3 and thus, a description thereof will be omitted.

The laser amplifying unit 320 includes a first beam splitter 323a, a first amplification medium 321a, a first mirror 322a, a second mirror 322b, a first lens 325a, a second lens 325b, a second amplification medium 321b, a first pumping lamp 325, a second beam splitter 323b, a first wave plate 324, a third mirror 322c, and a fourth mirror 322d. Although not shown, an SHG (not shown) as in FIG. 1 may be further included in the laser amplifying unit 320. The first beam splitter 323a transmits P-polarized light and reflects S-polarized light. Thus, the laser pulse supplied from the laser generating unit 310 is a P-wave as in the laser generating unit 310 shown in FIG. 1 and thus transmits the first beam splitter 323a as it is. Also, the first beam splitter 323a is arranged on the same axis as the proceeding direction of the laser source supplied from the laser generating unit 310. Of course, the arrangement of the first beam splitter 323a may be changed.

The first amplification medium 321a serves to amplify the laser pulse supplied from the laser generating unit 310. The first pumping lamp 326 illuminates the first amplification medium 321a so as to excite ions in the first amplification medium 321a. The first pumping lamp 326 is spaced apart from the first amplification medium 321a. The first amplification medium 321a is formed in a rod structure. The first amplification medium 321a is formed of Nd:YAG. However, the present invention is not limited thereto, and the first amplification medium 321a may be changed into Nd:GGG or Yd:LaCOB, other types, structures, and shapes as much as possible.

Also, the first amplification medium 321a is arranged on the same axis as the first beam spitter 323a. Thus, the laser pulse that transmits the first beam splitter 323a is firsts amplified while passing through the first amplification medium 321a.

The first mirror 322a is arranged to face the first beam splitter 323a with the first amplification medium 321a therebetween. The first mirror 322a reflects the laser pulse passing through the first amplification medium 321a to change the path of the laser pulse.

The second mirror 322b reflects the laser pulse having the path changed by the first mirror 322a to change the path again. The second mirror 322b is arranged on one side of the first mirror 322a.

The second amplification medium 321b serves to second amplify the laser pulse reflected from the second mirror 322b. The second amplification medium 321b is spaced apart from the first amplification medium 321a. The first pumping lamp 326 illuminates the second amplification medium 321b so as to excite ions in the second amplification medium 321b. The first pumping lamp 326 is spaced apart from the second amplification medium 321b. The first amplification medium 321b is formed in a rod structure. Also, the first amplification medium 321b is formed of Nd:YAG. However, the present invention is not limited thereto, and the second amplification medium 321b may be changed into Nd:GGG or Yb:LaCOB, other types, shapes and structures as much as possible.

In the present embodiment, the first pumping lamp 326 illuminates both the first amplification medium 321a and the second amplification medium 321b. However, the present invention is not limited thereto, and the first pumping lamp 326 has a structure including two lamps so that each lamp of the first pumping lamp 326 irradiates light to the first amplification medium 321a and the second amplification medium 321b. Also, a lamp for illuminating each of the first amplification medium 321a and the second amplification medium 321b may be separately arranged by one. In this case, the amplification pulse energy of the laser amplifying unit 320 further increases.

Also, the second amplification medium 321b is arranged on the same axis as the second mirror 322b. Thus, the laser pulse reflected from the second mirror 322b is second amplified while passing through the second amplification medium 321b.

The first lens 325a and the second lens 325b is arranged between the second mirror 322b and the second amplification medium 321b. The first lens 325a and the second lens 325b adjust the spatial size of the laser pulse reflected from the second mirror 322b.

The second beam splitter 323b is arranged to face the second mirror 322b with the second amplification medium 321b therebetween. Since the second amplified laser pulse is a P-wave, the second beam splitter 323b transmits the second amplified laser pulse.

The third mirror 322c reflects the laser pulse transmitting the second beam splitter 323b to change the path of the laser pulse. The third mirror 322c is arranged to face the second amplification medium 321b with the second beam splitter 323b therebetween.

The first wave plate 324 is arranged between the second beam splitter 323b and the third mirror 322c. The first wave plate 324 is formed as a half wave plate. Thus, the waveform of the laser pulse that passes through the first wave plate 324 is changed from the P-wave to the S-wave.

The third mirror 322c is arranged to face the second beam splitter 323b with the first wave plate 324 therebetween. Also, the third mirror 322c is arranged on one side of the first beam splitter 323a. The laser pulse having the path changed by being reflected from the third mirror 322c returns to the first beam splitter 323a and is reflected. The laser pulse reflected from the first beam splitter 323a is directed to the first amplification medium 321a.

The laser pulse that is third amplified while passing through the first amplification medium 321a is reflected from the first mirror 322a, and the path of the laser pulse is changed. The laser pulse having the path changed by being reflected from the first mirror 322a is reflected from the second mirror 322b, and the path of the laser pulse is changed, and the laser pulse is directed to the second amplification medium 321b.

The laser pulse that is fourth amplified while passing through the second amplification medium 321b is reflected by the second beam splitter 321b, and the path of the laser pulse is changed. Since the waveform of the laser pulse while passing through the first wave plate 324 has been changed to the S-wave, the laser pulse does not transmit the second beam splitter 323b but is reflected, and the path of the laser pulse is changed.

The fourth mirror 322d is arranged on one side of the second beam splitter 323b. The fourth mirror 322d is arranged on one side of the second beam splitter 323b. The fourth mirror 322d changes the path of the laser pulse reflected by the second beam splitter 323b and outputs the laser pulse.

The laser device for skin treatment 300 according to the present embodiment has an advantage of having a simpler structure than the laser device for skin treatment 200 of FIG. 6 and good amplification efficiency, because the number of amplification times is the same as four times compared to the laser device for skin treatment 200 of FIG. 6 and the number of wave plates is less than that of the laser device for skin treatment 200 of FIG. 6.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

By using the present invention, a laser device for skin treatment in which the wavelength of a laser generated by a laser generating unit can be conveniently varied by adjusting an operating temperature of a diode laser or a current value applied to the diode laser and a laser pulse having various durations can be output using a varied laser pulse, can be provided.

The invention claimed is:
1. A laser device, comprising:
a first diode laser device configured to vary at least one of a wavelength of a laser and a duration of a pulse to generate a laser pulse;
a laser amplifier configured to amplify the laser pulse from the first diode laser device;
and
a controller configured to control the first diode laser device and the laser amplifier to control at least one of the wavelength of the laser and the duration of the laser pulse output from the laser amplifier;
wherein the laser amplifier comprises:
a first amplification medium for first amplifying the laser pulse from the first diode laser device;
a first mirror arranged to reflect the laser pulse first amplified while passing through the first amplification medium and to return the first amplified laser pulse in a direction of the first amplification medium;
a first beam splitter arranged to face the first mirror with the first amplification medium therebetween and to adjust a path of the laser pulse second amplified while returning to and passing through the first amplification medium;
a first waveplate arranged between the first mirror and the first beam splitter to change a polarization or phase of the laser pulse;
a second mirror configured to transmit the laser pulse having the path adjusted by the first beam splitter to a second amplification medium, wherein the second amplification medium is spaced apart from the first amplification medium and is for third amplifying the laser pulse supplied from the second mirror;
a first pumping lamp spaced apart from the first amplification medium and the second amplification medium and configured to illuminate the first amplification medium and the second amplification medium;

a third mirror arranged to face the second mirror with the second amplification medium therebetween, to reflect the laser pulse third amplified while passing through the second amplification medium and to adjust a path of the third amplified laser pulse;

a fourth mirror configured to transmit the laser pulse having the path adjusted by the third mirror to a third amplification medium for fourth amplifying the laser pulse supplied from the fourth mirror:

a fifth mirror arranged to face the fourth mirror with the third amplification medium therebetween, to reflect the laser pulse fourth amplified while passing through the third amplification medium and to adjust a path of the fourth amplified laser pulse;

a sixth mirror configured to transmit the laser pulse having the path adjusted by the fifth mirror to a fourth amplification medium for fifth amplifying the laser pulse supplied from the sixth mirror;

a second pumping lamp spaced apart from the third amplification medium and the fourth amplification medium and configured to illuminate the third amplification medium and the fourth amplification medium; and a seventh mirror arranged to face the sixth mirror with the fourth amplification medium therebetween, to reflect the laser pulse passing through the fourth amplification medium and to adjust a path of the laser pulse.

2. The laser device of claim 1, further comprising:
a first diode laser driver corresponding to the first diode laser device and configured to vary a pulse duration of the first diode laser pulse.

3. The laser device of claim 1, further comprising:
one or more lenses arranged between the third mirror and the fourth mirror for adjusting a size of the laser pulse reflected from the third mirror.

4. The laser device of claim 1, wherein the first diode laser device comprises a first diode laser and a first thermostat, and wherein the controller is further configured to control the wavelength based on controlling the first thermostat to adjust a temperature of the first diode laser.

5. The laser device of claim 4, wherein the first diode laser device further comprises a temperature sensor configured to measure the temperature of the first diode laser and transmit measured temperature information to the controller.

6. The laser device of claim 1, wherein the first diode laser device comprises a first diode laser and a first current regulator, and wherein the controller is configured to control the wavelength based on controlling the current regulator to adjust a current applied to the first diode laser.

7. The laser device of claim 6, wherein the first diode laser device further comprises a first current sensor configured to measure the current applied to the first diode laser and transmit measured current information to the controller.

8. The laser device of claim 1, wherein the first diode laser device comprises:
a first diode laser; and
a first wavelength detection sensor configured to measure the wavelength;
wherein the controller is further configured to adjust the wavelength based on the measured wavelength being outside of a wavelength range.

9. A laser device, comprising:
a first diode laser device configured to vary at least one of a wavelength of a laser and a duration of a pulse to generate a laser pulse;
a laser amplifier configured to amplify the laser pulse from the first diode laser device; and
a controller configured to control the first diode laser device and the laser amplifier to control at least one of the wavelength of the laser and the duration of the laser pulse output from the laser amplifier;
wherein the laser amplifier comprises:
a first amplification medium for first amplifying the laser pulse;
a first mirror arranged to reflect the laser pulse first amplified while passing through the first amplification medium and to return the first amplified laser pulse in a direction of the first amplification medium;
a first beam splitter arranged to face the first mirror with the first amplification medium therebetween and to adjust a path of the laser pulse second amplified while returning to and passing through the first amplification medium;
a first waveplate arranged between the first mirror and the first beam splitter to change a polarization or phase of the passing laser pulse;
a second mirror configured to transmit the laser pulse having the path adjusted by the first beam splitter to a second amplification medium, wherein the second amplification medium is spaced apart from the first amplification medium and is for third amplifying the laser pulse supplied from the second mirror;
a first pumping lamp spaced apart from the first amplification medium and configured to illuminate the first amplification medium;
a second pumping lamp spaced apart from the second amplification medium and configured to illuminate the second amplification medium;
a third mirror arranged to face the second mirror with the second amplification medium therebetween, to reflect the laser pulse third amplified while passing through the second amplification medium and to adjust a path of the third amplified laser pulse:
a fourth mirror configured to transmit the laser pulse having the path adjusted by the third mirror to a third amplification medium for fourth amplifying the laser pulse supplied from the fourth mirror;
a fifth mirror arranged to face the fourth mirror with the third amplification medium therebetween, to reflect the laser pulse fourth amplified while passing through the third amplification medium and to adjust a path of the fourth amplified laser pulse:
a sixth mirror configured to transmit the laser pulse having the path adjusted by the fifth mirror to a fourth amplification medium for fifth amplifying the laser pulse supplied from the sixth mirror;
a third pumping lamp spaced apart from the third amplification medium and configured to illuminate the third amplification medium;
a fourth pumping lamp spaced apart from the fourth amplification medium and configured to illuminate the fourth amplification medium; and
a seventh mirror arranged to face the sixth mirror with the fourth amplification medium therebetween, to reflect the laser pulse passing through the fourth amplification medium and to adjust a path of the laser pulse.

* * * * *